(12) United States Patent
Graehlert et al.

(10) Patent No.: US 9,470,615 B2
(45) Date of Patent: Oct. 18, 2016

(54) METHOD AND APPARATUS FOR DETERMINING THE PERMEATION RATE OF BARRIER MATERIALS

(71) Applicant: Fraunhofer-Gesellschaft zur Foerderung der angewandten Forschung e.V., Munich (DE)

(72) Inventors: Wulf Graehlert, Dresden (DE); Harald Beese, Freital (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 192 days.

(21) Appl. No.: 14/178,634

(22) Filed: Feb. 12, 2014

(65) Prior Publication Data

US 2014/0223999 A1   Aug. 14, 2014

(30) Foreign Application Priority Data

Feb. 12, 2013   (DE) ........................ 10 2013 002 724

(51) Int. Cl.
*G01N 15/08*   (2006.01)
*G01N 21/3504*   (2014.01)
(Continued)

(52) U.S. Cl.
CPC ........ *G01N 15/082* (2013.01); *G01N 15/0806* (2013.01); *G01N 15/0826* (2013.01); *G01N 21/031* (2013.01); *G01N 21/33* (2013.01); *G01N 21/3504* (2013.01); *G01N 21/359* (2013.01); *G01N 21/3581* (2013.01); *G01N 2015/086* (2013.01); *G01N 2021/399* (2013.01)

(58) Field of Classification Search
CPC ..................................................... G01N 15/082
USPC ............................................................. 73/38
See application file for complete search history.

(56) References Cited

U.S. PATENT DOCUMENTS

| 3,498,110 A | 3/1970 | Brun |
| 3,902,068 A | 8/1975 | Wood |

(Continued)

FOREIGN PATENT DOCUMENTS

| DE | 1673032 A1 | 4/1971 |
| DE | 2514848 A1 | 10/1975 |

(Continued)

*Primary Examiner* — John Fitzgerald
*Assistant Examiner* — David Z Huang
(74) *Attorney, Agent, or Firm* — Jacobson Holman, PLLC.

(57) ABSTRACT

A method and an apparatus for determining the permeation rate of barrier materials, with which in a measuring chamber (8.7) which has at least two shut-off elements (81; 8.2) for opening and closing, a concentration of at least one permeate is determined which, present as a test gas with a constant concentration in a test gas chamber (8.3), is permeated into the measuring chamber (8.7) through a barrier element (8.5) which is arranged between the test gas chamber (8.3) and the measuring chamber (8.7) and which has a known permeable surface (A). In this respect, the permeation rate is calculated using an enriching time (tA) and using a purge time (tS) determined using a first measurement variant in a process step (i) and the course of the permeate concentration (c) determined during the purge time (tS) or using a course of the permeate concentration (c) determined using a second measurement variant in a process step (i) during a predefinable purge time (tvS) and using the predefinable purge time (tvS) and a predefinable enriching time (tvA) using an equation.

12 Claims, 5 Drawing Sheets

Figure 1A:
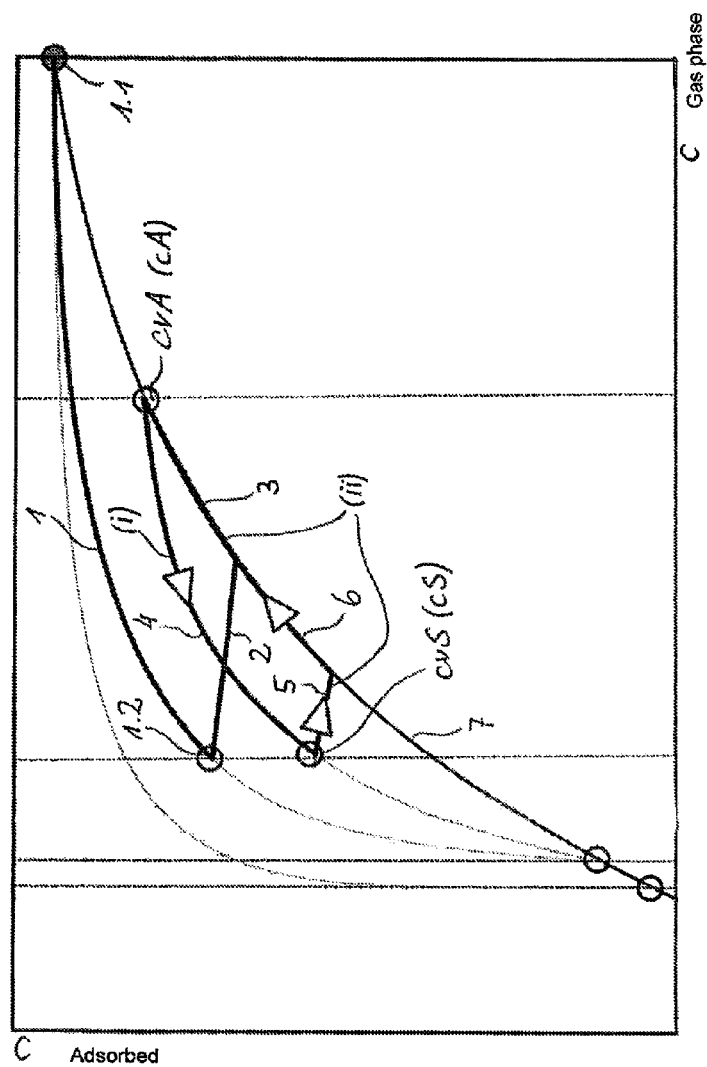

(51) Int. Cl.
  *G01N 21/03* (2006.01)
  *G01N 21/33* (2006.01)
  *G01N 21/3581* (2014.01)
  *G01N 21/359* (2014.01)
  *G01N 21/39* (2006.01)

(56) References Cited

U.S. PATENT DOCUMENTS

| | | | |
|---|---|---|---|
| 4,112,736 A * | 9/1978 | Wheldon | G01N 7/10 73/31.04 |
| 4,852,389 A | 8/1989 | Mayer et al. | |
| 4,944,180 A | 7/1990 | Tou et al. | |
| 5,591,898 A | 1/1997 | Mayer | |
| 5,817,924 A | 10/1998 | Tuomela et al. | |
| 6,964,191 B1 | 11/2005 | Tata | |
| 8,596,110 B2 * | 12/2013 | Rahman | G01N 13/04 73/38 |
| 2004/0123646 A1 | 7/2004 | Echigo et al. | |
| 2007/0227233 A1 | 10/2007 | Norenberg | |
| 2008/0118418 A1 * | 5/2008 | Morita | B01D 5/0054 422/255 |
| 2010/0294025 A1 | 11/2010 | Omori et al. | |

FOREIGN PATENT DOCUMENTS

| | | |
|---|---|---|
| DE | 102007014182 A1 | 12/2007 |
| DE | 10 2007 026 073 A1 | 11/2008 |

* cited by examiner

METHOD AND APPARATUS FOR DETERMINING THE PERMEATION RATE OF BARRIER MATERIALS

The invention relates to a method for determining the permeation rate of barrier elements as well as to an apparatus for carrying out the method.

Barrier materials having different permeation rates are being used in an every larger range of applications to reduce the gas exchange between media or between objects and their environment; for example, for the packaging of foodstuffs or medication or for the packaging of electronic components. Barrier materials having very low permeations rates are in particular in demand for organic electronics, for example for organic LEDs, organic photovoltaics or vacuum insulated panels (VIPs) since the quality and service life of these elements depend on the protection from moisture. As a consequence of the development of barrier materials having very low permeation rates, measurement processes are required with which permeation rates in the range from $10^{-5}$ to $10^{-6}$ gm$^{-2}$d$^{-1}$ can be determined reliably and simply.

A number of measurement systems having a plurality of material-specific and non-material specific sensors are already available for this purpose. Measuring methods are thus known, for example, in which a test gas permeates from a first chamber through a barrier material into a second, closed chamber and in so doing the increase in the permeation concentration in the gas phase of the closed chamber is measured over a specific time. This method is, however, prone to error due to different influences. For example, the time-wise increase in the permeation concentration is neither constant nor proportional to the permeation rate. Such errors in particular occur with very small permeation concentrations to be determined since the molecules of the permeate interact with the solid body surfaces within the closed chambers. Particularly on the determination of very small permeate concentrations, a non-consideration of these effects necessarily results in very error-prone measurement results. Measuring methods are therefore required with which in particular condensable gases can be determined without any influence from their adsorption and desorption properties.

In the already known Lyssy method, a humidity sensor measures the increase in relative humidity from, for example, 9.9% to 10.1% in a closed measurement chamber. The measurement chamber is subsequently purged down to a lower limit of the measurement range and a certain number of underdrying cycles for conditioning the measuring cell are performed before a new measurement cycle is started. If the increases of a plurality of measurement cycles coincide in this process, a stationary state can be assumed and the permeation rate through the barrier element can be determined. The measurement range of the water vapor permeability is, however, in a range between 0.03 to 10,000 gm$^{-2}$d$^{-1}$ and is thus too high by several orders of magnitude to be able to determine very low permeation rates.

Other measuring methods such as the calcium mirror test or radiometric methods require a time-consuming sample preparation and long measuring times due to the principle.

A very sensitive arid simultaneously simple and robust measurement technology for determining the permeation rate, for example of water vapor in the range $<10^{-4}$ gm$^{-2}$d$^{-1}$ is not known.

It is therefore the object of the invention to provide an alternative and simple method for determining the permeation rate of barrier materials whose measurement error can in particular be kept low in the determination of particularly small permeation rates.

The object is satisfied in accordance with the invention by a method in accordance with claim 1. Further developments of the method in accordance with the invention can be realized using features defined in the subordinate claims.

In the method in accordance with the invention for determining the permeation rate of barrier materials, in a measuring chamber which has at least two shut-off elements for opening and closing, a concentration of at least one permeate is determined which, present as a test gas with a constant concentration in a test gas chamber, is permeated into the measuring chamber through a barrier element which is arranged between the test gas chamber and the measuring chamber and which has a known permeable surface (A). In this respect, in a process step (i), in a first measurement variant, once a predefinable upper switchover concentration (cvA) has been reached or, in a second measurement variant, once a predefinable enriching time (tvA) has been reached, the measuring chamber is purged with a constant permeate-free purge gas volume flow ($\dot{V}$) by opening the shut-off elements, with the permeate concentration (c) in the open measuring chamber dropping as a result of the purging. In this respect, the course of the falling permeate concentration (c) in the first measurement variant is determined up to the reaching of a predefinable lower switchover concentration (cvS), with the purge time (tS) additionally being determined. In the second measurement variant, the course of the falling permeate concentration (c) is determined up to the reaching of a predefinable purge time (tvS).

Furthermore, in a process step (ii), in the first measurement variant, once the predefinable lower switchover concentration (cvS) has been reached or, in the second measurement variant, once the predefinable purge time (tvS) has been reached, the measuring chamber is closed by closing the shut-off elements, with the permeate concentration in the closed measuring chamber increasing as a consequence of the permeation. In this respect, in the first measurement variant, an enrichment time (tA) up to the reaching of the predefinable upper switchover concentration (cvA) is determined. Subsequently, in the first measurement variant with the purge time (tS) determined in process step (i) and with the course of the permeate concentration (c) determined during the purge time (tS) and the enriching time (tA) determined in process step (ii) or, in the second measurement variant with the course of the permeate concentration (c) determined in the process step (i) during the predefinable purge time (tvS), the predefinable purge time (tvS) and the predefinable enriching time (tvA), the permeation rate (P) of the barrier element is calculated using the equation $$P = \frac{\int (\varphi(t) \cdot \dot{V}) dt \cdot M \cdot p}{R \cdot T \cdot t_{total} \cdot A} \quad (1)$$

where $t_{total}$ is the sum of the purge time (tS) and of the enriching time (tA) for the first measurement variant and is the sum of the predefinable purge time (tvS) and of the predefinable enriching time (TvA) for the second measurement variant; M is the molar mass of the permeate; p is the maintained pressure, R is the general gas constant; and T is the temperature maintained during process steps (i) and (ii).

That portion of the test gas is to be understood as the permeate which moves during the permeation from the test gas chamber, in which a constant concentration of the test gas is present, through the barrier element into the measuring chamber. In this respect, the predefinable upper and lower switchover concentrations represent the respective maximum or minimal concentration of the permeate which can be reached in the measuring chamber.

The purge time (tS) is to be understood as the time period which is required at the settable purge gas volume flow ($\dot{V}$) to reduce the permeate concentration (c) in the measuring chamber, starting from the predefinable upper switchover concentration (cvA), down to the predefinable lower switchover concentration (cvS). The enriching time (tA) is the time period which is required with a closed measuring chamber until, starting from the predefinable lower switchover concentration (cvA), the permeate concentration (c) in the measuring chamber reaches the value of the predefinable upper switchover concentration (cvA) as a consequence of the permeation through the barrier element. This means that the opening of the shut-off elements is carried out at the predefinable upper switchover concentration (cvA) and the closing of the shut-off elements is carried out at the predefinable lower switchover concentration (cvS).

Provision is alternatively made with the second measurement variant that the measuring chamber is purged (i) with a time limitation for a predefinable purge time (tvS) with the permeate-free purge gas volume flow ($\dot{V}$) in process step (i) and remains closed for a predefinable enriching time (tvA) in process strep (ii). In this respect, in the second measurement variant, an upper switchover concentration value (cA) is adopted at the end of the predefinable enriching time (tvA) and a lower switchover concentration value (cS) is adopted at the end of the predefinable purge time (tvS).

While the upper and lower switchover concentrations (cvA, cvS) are predefined in the first measurement variant, the purge time (tvS) and the enriching time (tvA) are predefined in the second measurement variant.

In order also to take account of the quantity of the permeate permeating into the measuring chamber during the purge time (tS) or during the predefinable purge time (tvS), not only the enriching time (tA) or the predefinable enriching time (tvA) is considered in equation (1) for calculating the permeation rate (P), but also the purge time (tS) or the predefinable purge time (tvS).

The method can advantageously be carried out starting with process step (i) or starting with process step (ii). A change from process step (i) to process step (ii) and vice versa can be carried out after reaching the predefinable lower switchover concentration (cvS) or the predefinable upper switchover concentration (cvA) or after reaching the predefined purge time (tvS) or the predefined enriching time (tvA).

The permeation rate (P) can be respectively determined from at least one measurement cycle comprising at least one process step (i) and at least one process step (ii). The measurement cycle can consequently also be formed from a plurality of process steps (i) and (ii).

In the closed measuring chamber, i.e. the shut-off elements are closed and the purge gas volume flow ($\dot{V}$) is interrupted, the permeate concentration rises as a consequence of the permeation through the barrier element. A portion of the permeate adsorbs at the inner solid body surfaces of the measuring chamber and a further portion remains in the gas phase. In this respect, a state of equilibrium can be adopted between the permeate adsorption and the permeate desorption in the closed measuring chamber. Since this state of equilibrium is practically present, the increase in the concentration of the adsorbing permeate and the concentration rise of the permeate in the gas phase follows a so-called system isotherm which can be understood as a specific isotherm characteristic for each examination sample, i.e. for each barrier element, for each apparatus and/or for each test gas, at which isotherm characteristic a concentration value of the permeate in the gas phase can be associated with each concentration value of the adsorbed permeate. Accordingly a state can be understood as the state of equilibrium (SOE) which is reached when a permeate concentration rise in the measuring chamber runs along the isotherm characteristic.

The state can be understood as the stationary state which is reached when a constant permeation rate through the barrier element has been adopted. It should be ensured in this respect that a constant concentration of the test gas is present in the test gas chamber.

Due to the purge gas volume flow ($\dot{V}$) which flows through the measuring chamber during the purge time (tS) or the predefinable purge time (tvS) in process step (i), the permeate concentration of the gas phase of the measuring chamber first drops faster than the concentration of the permeate adsorbed at the solid body surface, whereby the SOE in the measuring chamber is cancelled. In this respect, the permeate concentration, i.e. the adsorbed portion and the portion in the gas phase, follows a transient isotherm characteristic whose course depends, starting from its starting point on the system isotherm characteristic, i.e., for example, starting from the predefinable upper switchover concentration (cvA) and the purge gas volume flow ($\dot{V}$).

The interruption of the purge gas volume flow ($\dot{V}$) caused in process step (ii) by the closing of the shut-off elements effects an increase in the permeate concentration in the gas phase as a consequence of the permeation through the barrier element. The permeate concentration of the gas phase increases continuously. The portion of the adsorbed gas also reduces slightly due to desorption processes up to the reaching of a point of intersection with the isotherm characteristic. Once the point of intersection with the isotherm characteristic has been reached, the permeate concentration increases along the isotherm characteristic. This means that the SOE has been almost restored.

The permeation rate should preferably only be determined when the stationary state has been adopted. This is the case when a stable concentration gradient of the permeate has formed in the barrier or in a foil configured as a barrier, i.e., the humidity has broken through and the permeation rate is constant. Due to the small concentration change in the measuring chamber, which only amounts to a few ppm, the concentration difference to the test gas side remains practically uninfluenced.

A purging and enriching step should have been carried out at least once directly before the carrying out of the actual first measurement cycle so that a presence of the state of equilibrium (SOE) can be assumed.

Only when the stationary state has been reached at least approximately can the permeation rate be reliably determined.

To check the presence of the stationary state with the first measurement variant, the measurement cycle can also be repeated so often until the total cycle time resulting from the sum of the enriching time (tA) and the purge time (tS) coincides with the measurement cycle directly before it in time or differs from it by a maximum of twice the measurement uncertainty.

The presence of the stationary state can be checked using the second measurement variant in that the measurement cycle is repeated so frequently until the lower switchover concentration value (cS) coincides with that of the measurement cycle directly before it in time or differs from it by a maximum of twice the measurement uncertainty and simultaneously the difference between the upper switchover concentration value (cA) and the lower switchover concentration value (cS) coincides with that of the measurement cycle directly before it in time or differs from it by a maximum of twice the measurement uncertainty.

A parameter is designated as the measurement uncertainty which is associated with the measurement result and which characterizes the scatter of the measured values which can reasonably be associated with the measurement parameter. A simple measurement uncertainty means a reliability uncertainty of 68.3%; twice a measurement uncertainty means a reliability uncertainty of 95.4%. (In accordance with GUM "Guide of the Expression of the Uncertainty in Measurement", issued by ISO; prior standard DIN 13005/(in Willfried Schwarz "The correct interpretation of exactness measurements", DVW Periodicals, Vol. 46, 2004).

Provision can, however, also be made to repeat the measurement cycle so frequently until the respective determined permeation rate (P) of a measurement cycle coincides with that of the measurement cycle directly before it in time or differs from it by a maximum of 20%.

The purge gas volume flow ($\dot{V}$) can be set and should be the same in measurement cycles which follow one another in process steps (i) and which are carried out starting with process step (ii).

In the stationary state, a closed loop can be adopted between the respective switchover concentrations (cvA, cvS) or switchover concentration values (cV, cS) due to the repetition of the measurement cycles.

The lower detection limit of the permeation rate determination can be decoupled from a technically induced lower sensor detection limit by this procedure. The process steps (i) and process steps (ii) used for calculating the permeation rate (P) in this respect do not necessarily have to follow one another; an integration can rather be carried out over several of the process steps (i), with the integration correspondingly relating to the total purge time and with the total time ($t_{total}$) corresponding to the sum of all considered purge times and enriching times.

In the carrying out of a first measurement cycle comprising the process steps (i) and (ii), the measuring chamber should be prepurged with the permeate-free purge gas volume flow ($\dot{V}$), preferably in a measurement cycle which starts with the process step (i) by a preconditioning of the measuring chamber at least once by opening the shut-off elements, preferably until the predefinable lower switchover concentration (cvS) or the predefinable purge time (tvS) has been reached, and the measuring chamber should subsequently be closed again by closing the shut-off elements. The starting point of the preconditioning of the measuring chamber can in this respect lie on the isotherm characteristic whose permeate concentration is larger than the upper switchover concentration (cvA). The starting point of the preconditioning of the measuring chamber can thus also lie in the range of atmospheric conditions.

During the preconditioning of the measuring chamber, the measuring chamber should be insulated from the environmental atmosphere and the temperature should be kept constant.

In the stationary state, adsorption processes and desorption processes within the closed loop cannot falsify the measurement result since ultimately the measurement principle is based on just these effects. In a measurement cycle carried out within the closed loop, advantageously only that quantity of the permeate gas is thereby first detected which actually permeates through the barrier element during the observation time ($t_{total}$), which results from the sum of the purge time (tS) and the enriching time (tA) or from the sum of the predefinable purge time (tvS) and the predefinable enriching time (tvA).

The described method can preferably be carried out at a temperature in the range between 10° C. and 80° C. for all condensable gases and vapors as the test gas or permeate respectively. The preferred test gas is water vapor, with care having to be taken that a permeate-free purge gas volume flow ($\dot{V}$) or, in the case of water vapor as a test gas, a dry purge gas volume flow ($\dot{V}$) is used.

A higher precision of the permeation rate determination can be achieved in that the mean value of the respective determined permeation rates is determined. Under the precondition of the closed loop, an approximate value of the permeation rate to be expected can be estimated to reduce the measurement error in a following measurement cycle on the basis of which, for example, the predefinable upper switchover concentration (cvA) and/or the predefinable lower switchover concentration (cvS) for subsequent measurement cycles can be limited.

The precision of the permeation rate determination can be increased when the difference between the predefinable upper switchover concentration (cvA) and the predefinable lower switchover concentration (cvS) is increased or when, in the second measurement variant, the predefinable purge time (tvS) and/or the predefinable enriching time (tvA) is extended.

Furthermore, a reduction in the purge gas volume flow ($\dot{V}$) can contribute to increasing the measurement precision. A smaller measurement error can also be achieved by the combination of the named measures.

An increase in the measuring precision can also be achieved by an optimization of the working point which lies in a region in which the gas concentration measurement has its highest sensitivity. In this respect, the optimization of the working point is to be understood as an adaptation of the predefinable upper and lower switchover concentrations (cvA, cvS) or as an adaptation of the predefinable purge times and enriching times (tvS, tvA).

A non-invasive, preferably optical and/or capacitive measurement method which does not consume and/or change the permeate should preferably be used for the detection of the permeate concentration in the gas phase of the measuring chamber. In this respect, a permeate concentration in the range from 0.01 ppm to 1000 ppm should be able to be determined using the named measurement method. A laser-based measurement method can preferably be used, particularly preferably a laser diode spectroscopy method, in which a laser beam is emitted which has an emission wavelength preferably coordinated with an absorption line of the permeate to be detected. In this respect, there is the possibility that the laser is simply guided through the measuring chamber. The measuring chamber can, however, also be configured as a multiple reflection measurement cell in which a laser is led through the gas phase of the measuring chamber, for example deflected by a plurality of mirrors, a plurality of times. The source of such a laser can be arranged inside the measuring chamber or outside, with the laser beam being coupled into the measuring chamber through windows. In this respect, a laser source can be used which emits a laser beam having a plurality of different wavelengths. Such laser sources are moreover advantageous in which the wavelength of the emitted laser beam can be varied, preferably in operation. A plurality of laser sources can also be used, with a plurality of laser beams being emitted having wavelengths different from one another.

The detection of the permeate concentration can, however, also be carried out using at least one gas sensor which is specific to the permeate and which is arranged within the measurement cell. The use of a plurality of gas sensors has the advantage that a plurality of different permeates can be determined simultaneously. There is, however, also the possibility of the use of multichannel gas sensors, for example of a UV, VIS, NIR, MIR, quantum cascade laser spectrometer or of a terahertz spectrometer with which a plurality of permeates can likewise be determined simultaneously.

Furthermore, a non-specific pressure sensor can be used in conjunction with a vacuum pump, with the purge gas volume flow being replaced with a pump volume flow. The pump volume flow can in this respect be determined, for example, via a pressure drop measurement over a diaphragm. In this respect, the permeate is the dominating species in the pump volume flow so that the pump volume flow can be considered as a permeate volume flow in simplified terms.

The predefinable upper switchover concentration (cvA) and the predefinable lower switchover concentration (cvS) can be selected such that they lie in a measurement range or working range ideal for the used measurement process or for the used gas sensor. The switchover concentrations can, however, preferably be selected so that they do not fall below a lower permeate concentration limit at 0.01 ppm, and do not exceed an upper permeate concentration limit at 1000 ppm. 100 ppm should particularly preferably be selected for the predefinable upper switchover concentration (cvA). Since the predefinable switchover concentrations (cvA, cvS) can be fixed in a measurement range or working range ideal for the sensor(s) used, a particularly high precision of the permeation measurement can be achieved which can be higher than the precision of the classical carrier-gas based permeation measurement at the detection limit of the sensor used or makes a determination of the permeation rate possible at all in comparison with a classical carrier-gas based permeation measurement.

An apparatus in accordance with the invention for carrying out the method in accordance with the invention has a measuring chamber having at least two shut-off elements for opening and closing. The apparatus furthermore comprises a detection unit with which a concentration of at least one permeate can be determined which, present as a test gas with a constant concentration in test gas chamber, permeates into the measuring chamber through a barrier element which is arranged between the test gas chamber and the measuring chamber and which has a known permeable surface (A), with the measuring chamber being able to be purged with a constant test-gas free purge gas volume flow (V̇) once a predefinable upper switchover concentration (cvA) has been reached or once a predefinable enriching time (tvA) has been reached by opening the shut-off elements, as a consequence of which the permeate concentration (c) in the measuring chamber drops and the course of the permeate concentration (c) as well as, when the upper switchover concentration (cvA) is predefined, the purge time (tS) up to the reaching of the predefinable lower switchover concentration (cvS) can be determined and with the measuring chamber being able to be closed once a predefinable lower switchover concentration (cvS) or a predefinable purge time (tvS) has been reached by closing the shut-off elements, with the permeate concentration in the closed measuring chamber rising as a consequence of the permeation and the enriching time (tA) up to the reaching of the predefinable upper switchover concentration (cvA) being able to be determined.

The proposed method can be used without any complex sample preparation in a simple manner under the above-described preconditions, i.e. the sensor working non-invasively is in the measuring chamber, with further already existing two-chamber measuring systems.

The present invention will be explained in more detail in the following with reference to diagrams and to an embodiment.

Figure 1B:
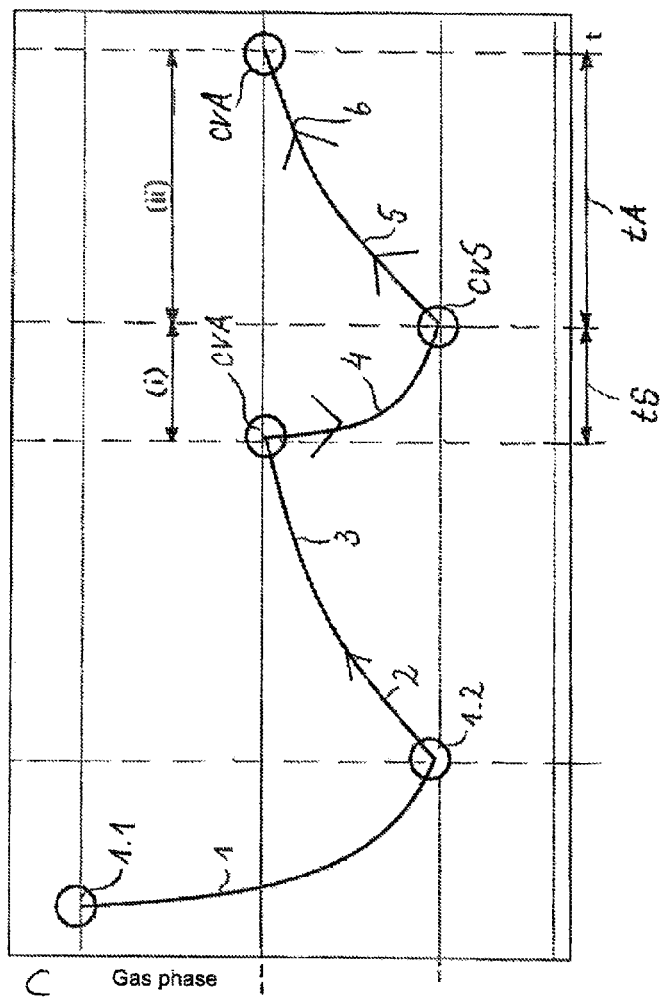
Figure 1C:
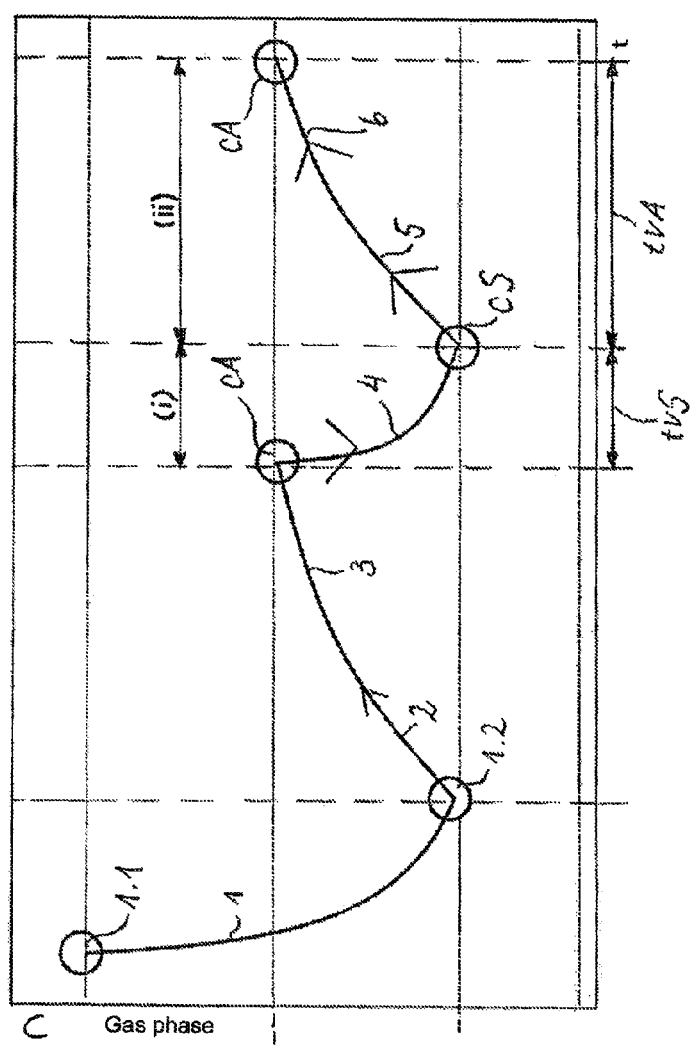
Figure 1D:
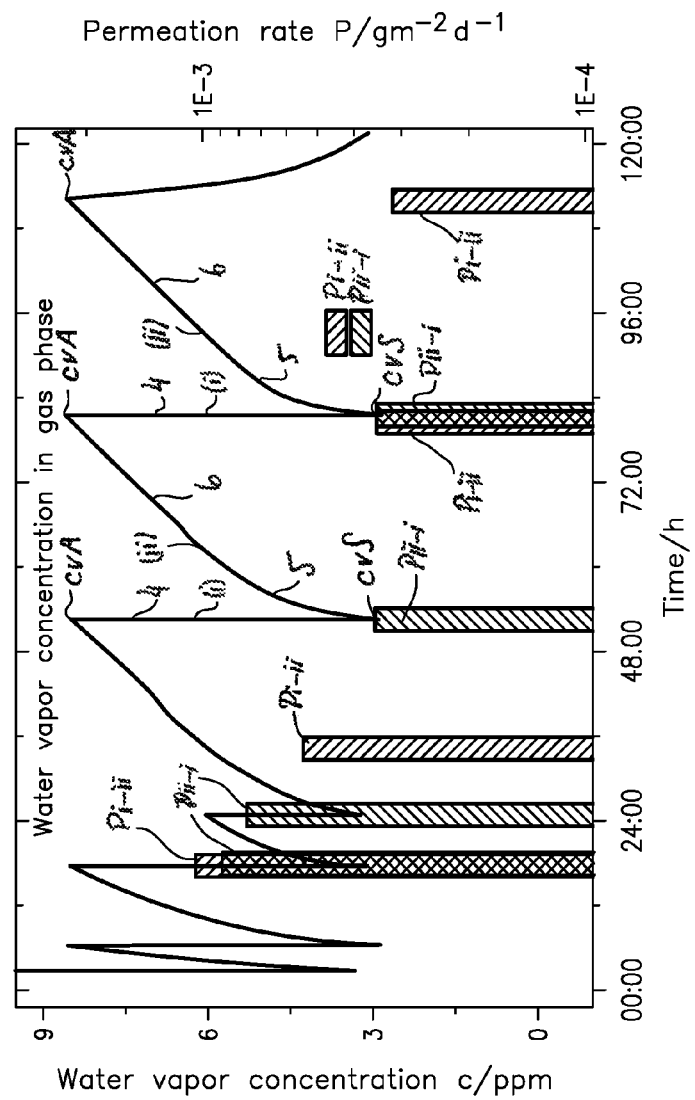
Figure 2:
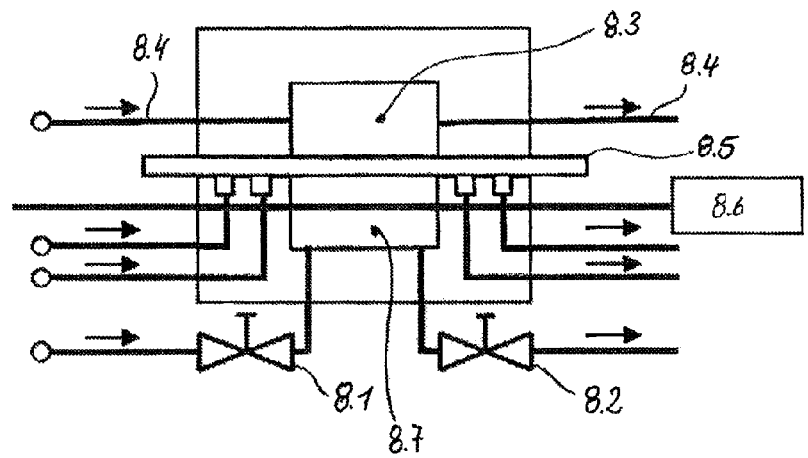
Figure 3:
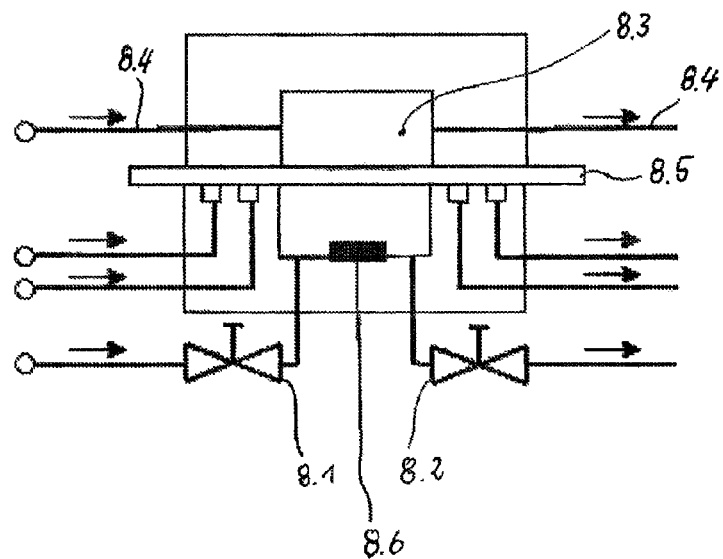

There is shown:

FIG. 1a: the general method principle with reference to the time course of a measurement in a schematic state diagram in the first and second measurement variants with reference to the connection between the concentration of the adsorbed permeate and the permeate concentration in the gas phase during the permeation of a test gas into the measuring chamber starting from atmospheric conditions; and FIG. 1b: a schematic representation of a permeate gas concentration time course in a measuring chamber in the first measurement variant; and FIG. 1c: a schematic representation of a permeate gas concentration time course in a measuring chamber in the second measurement variant; and FIG. 1d: a representation of a permeate gas concentration time course of following measurement cycles determined using the first measurement variant together with the respective determined permeation rates; and FIG. 2: a schematic sectional representation of an apparatus for carrying out the method in accordance with the invention with an (optical) irradiation process; and FIG. 3: a further schematic sectional representation of the apparatus for carrying out the method in accordance with the invention with a capacitive gas sensor.

The concentration changes of the permeate in the gas phase of a measuring chamber 8.7 occurring during the method in accordance with the invention can be understood with reference to the schematic diagrams of the time course shown in the FIGS. 1a, 1b and 1c by coinciding reference symbols, with the reference symbols cA and cS shown in brackets in FIG. 1a applying to the second measurement variant.

The state diagram shown in FIG. 1a schematically describes the connection between the concentration of the permeate adsorbed at the solid body surfaces and the permeate concentration in the gas phase during the preconditioning of the measuring chamber and the process steps (i) and (ii). In this respect, the axis marked by $C_{adsorbed}$ corresponds to the concentration of the permeate adsorbed at the solid body surfaces and the axis marked by $c_{gas\ phase}$ corresponds to the permeate concentration present in the gas phase. The system isotherm characteristic marked by the reference numeral 7 describes the function of the state of equilibrium from the permeate concentration in the gas phase to the concentration of the permeate adsorbed at the solid body surfaces in the measuring chamber 8.7. In this respect, the specific adsorption behavior of each material, such as the cell wall material, in contact with the permeate, the materials of the optical elements (windows, mirror, fixing component), sealing materials and the sample, i.e. the barrier material itself, is taken into account.

The concentration course during the purging within the preconditioning of the measuring chamber 8.7 which follows a transient isotherm characteristic as a result of the purging is marked by the reference numeral 1 in FIG. 1a. Furthermore, the curve course marked by the reference numeral 2 shows the increase in the permeate concentration in the gas phase without any significant change in the concentration of the adsorbed permeate directly after dosing the measuring chamber 8.7 at point 1.2. Since the surface covering in this state is larger than the surface covering in the state of equilibrium with the same permeate concentration in the gas phase, both desorbed permeate and the directly permeated permeate remain exclusively in the gas phase, whereby the concentration increase marked by the reference numeral 2 only extends up to a point of intersection with the system isotherm characteristic 7 with a small drop, i.e. almost without change in the concentration of the adsorbed permeate. From there, the concentration course of the permeate follows the system isotherm characteristic 7, i.e. In the state of equilibrium up to reaching a predefinable upper switchover concentration cvA. In the case that the second measurement variant is carried out in which the enriching time tvA is predefined, the concentration course of the permeate follows the system isotherm characteristic 7, with the starting point of a process step (i) being determined after a freely selectable time. At the end of the predefinable enriching time, an upper switchover concentration value cA is reached in this respect which is shown enclosed in brackets in FIG. 1*a*.

The curve extent marked by the reference numeral 4 in FIG. 1*a* describes the concentration change of the permeate in the measuring chamber 8.7 which is caused by the purge gas volume flow ($\dot{V}$) with an open measuring chamber 8.7 during process step (i) until the predefinable lower switchover concentration cvS is reached in the first measurement variant or until a predefinable purge time tvS is reached in the second measurement variant, with the lower switchover concentration value cS enclosed in brackets in FIG. 1*a* being adopted at the end of the predefinable purge time tvS.

The concentration increase of the permeate which occurs as a result of the permeation in process step (ii) after the closing of the measuring chamber 8.7 is marked by the reference numeral 5. When a point of intersection with the system isotherm characteristic 7 is reached, the concentration of the permeate increases along the system isotherm characteristic 7. From the point of intersection with the system isotherm characteristic 7 at which the concentrations of the adsorbed permeate and the permeate in the Bas phase are present in the state of equilibrium (SOE), the curve course is marked by the reference numeral 6. In the first measurement variant, process step (ii) ends on a reaching of the predefinable upper switchover concentration cvA. In the second measurement variant, process step (ii) ends on a reaching of the predefinable enriching time tvA, with the upper switchover concentration value cA being reached.

FIG. 1*b* and FIG. 1*c* show a schematic representation of a permeate gas concentration time course in a measuring chamber 8.7 in the first and second measurement variants respectively. The course curve shown by reference numerals 1, 2 and 3 designates a concentration change of a permeate which occurs in the gas phase of the measuring chamber 8.7 during a preconditioning of the measuring chamber 8.7. Reference numeral 4 describes the course of the permeate concentration in the measuring chamber 8.7 during a process step (i). Reference numerals 5 and 6 describe the course of the permeate concentration in the measuring chamber 8.7 during a process step (ii). During the two process steps (i) and (ii), the test gas which is present in a constant concentration in the test gas chamber 8.3 permeates continuously from the test gas chamber 8.3 through a barrier element 8.5 which is arranged between the test gas chamber 8.3 and the measuring chamber 8.7 and which has a known permeable surface A into the measuring chamber 8.7 and there effects the change in the permeate concentration.

The curve section marked by the reference numeral 1 in FIGS. 1*b* and 1*c* describes a purging within the framework of the preconditioning of the measuring chamber 8.7 at which the previously opened measuring chamber 8.7 is purged by a purge start permeate concentration 1.1 starting with a permeate-free purse gas volume flow ($\dot{V}$) until a purge end permeate concentration has been reached marked by the reference numeral 1.2. Starting from the purge end permeate concentration 1.2, at which the purge gas volume flow ($\dot{V}$) is interrupted and the measuring chamber 8.7 is closed again, the permeate concentration in the measuring chamber 8.7 rises due to the continuous permeation of the test gas as can be understood with reference to the curve course described by the reference numerals 2 and 3. The preconditioning of the measuring chamber 8.2 is carried out equally for both measurement variants.

As can be seen from FIG. 1*b* which shows the first measurement variant, the curve course described by reference numerals 2 and 3 reaches the predefinable upper switchover concentration cvA at which process step (i) starts. The curve course which is marked by reference numeral 4 and which corresponds to a permeate concentration course c describes the reduction of the permeate concentration in the gas phase of the measuring chamber 8.7 during process step (i) in which the measuring chamber 8.7 is purged with a constant permeate-free purge gas volume flow ($\dot{V}$) until reaching a predefinable lower switchover concentration cvS. The curve section ends on the reaching of a predefinable lower switchover concentration cvS at which the purge gas volume flow ($\dot{V}$) is interrupted in that the measuring chamber 8.7 is closed. The purge time from reaching the predefinable upper switchover concentration cvA until reaching the predefinable lower switchover concentration cvS is marked by the reference symbol tS. Reference numerals 5 and 6 describe the curve course of the permeate concentration during a process step (ii) at which the permeate concentration in the closed measuring chamber 8.7 increases as a consequence of the permeation through the barrier element 8.5. The enriching time starting from the predefinable lower switchover concentration cvS until reaching the predefinable upper switchover concentration cvA is described by the reference symbol tA.

In the second measurement variant shown by FIG. 1*c*, the curve course described by reference numerals 2 and 3 reaches the starting point of process step (i) after a freely selectable enriching time (not shown). In this respect, the starting point in the present case corresponds to the upper switchover concentration value cA. The curve course which is marked by reference numeral 4 and which corresponds to a permeate concentration course c describes the reduction of the permeate concentration in the gas phase of the measuring chamber 8.7 during process step (i) in which the measuring chamber 8.7 is purged with a constant permeate-free purge gas volume flow ($\dot{V}$) during the predefinable purge time tvS. The curve section ends on reaching the predefinable purge time tvS, with the lower switchover concentration value cS being reached. The purge gas volume flow ($\dot{V}$) is interrupted in that the measuring chamber 8.7 is dosed. Reference numerals 5 and 6 describe the curve course of the permeate concentration during a process step (ii) at which the permeate concentration in the closed measuring chamber 8.7 increases as a consequence of the permeation through the barrier element 8.5. In this respect, process step (ii) ends after termination of the predefinable enriching time tvA, with the starting point of process step (i) being reached on reaching of the upper switchover concentration value cA.

FIG. 1d shows a representation of a permeate gas concentration time course of mutually following measurement cycles determined using the first measurement variant together with the respective permeation rates which are each determined per measurement cycle and which are shown as hatched columns. In this respect, columns bearing the symbol Pi-ii each show the permeation rates which were determined on a measurement cycle started using process step (i). In contrast, the columns in which the permeation rates were each determined with a measurement cycle started using process step (ii) are marked by the symbol Pii-i. The left hand vertical axis has a scale in ppm of the permeate concentration (water vapor concentration) in the measurement chamber 8.7, with the right hand vertical axis having a scale of the permeation rate in $gm^{-2}d^{-1}$. The permeate concentrations and respectively determined permeation rakes shown in FIG. 1d are concrete results which were determined using an apparatus described in the following and using an example of the method in accordance with the invention described in detail further below.

FIG. 2 shows a schematic sectional representation of an example apparatus for carrying out the method in accordance with the invention. The apparatus comprises a measuring chamber 8.7 having two shut-off elements 8.1 and 8.2 for opening and closing, a test gas chamber 8.3 having a constant test gas concentration, a barrier element 8.5 arranged between the test gas chamber 8.3 and the measurement chamber 8.7 and having a known surface A and a detection device 8.6 arranged at the measuring chamber 8.7 for detecting a test gas permeating from the test gas chamber 8.3 through the barrier element 8.5 into the measuring chamber 8.7. In the present example, the detection device is designed as a laser diode spectroscope, with a laser beam being guided through the measuring chamber 8.7 through windows not shown here.

FIG. 3 shows an apparatus as in FIG. 2 with the difference that the detection device 8.6 is designed as a capacitive gas sensor which is arranged within the measuring chamber 8.7.

In the present example apparatus of FIGS. 2 and 3, the shut-off elements 8.1 and 8.2 are designed as valves. However, ball cocks, sliders or MFCs (mass flow controllers) can also be used.

The barrier element 8.5 can, for example, be materials such as metal foils, (metal) coated polymer foils as well as their laminates or complex multilayer systems comprising polymers, metals and inorganic materials (oxides, nitrides, carbides, etc.). In the following embodiment, POLO® foil, comprising a 75 μm PET Melinex 400CW substrate foil and a composite layer of 180 nm zinc tin oxide, 800 nm ORCOMER®, 180 nm zinc tin oxide and 800 nm ORCOMER®, was used as a barrier material which has a total thickness of 77 μm.

In the apparatus shown in FIG. 2 for carrying out the method in accordance with the invention, the concentration of water vapor in the gas phase is determined in the measuring chamber 8.7, which has a diameter of 131 mm and a height of 9 mm, using a detection device 8.6 which is designed as a laser diode spectrometer in the present case, said water vapor permeating into the measuring chamber 8.7 through a barrier element 8.5 arranged between the test gas chamber 8.3 and the measuring chamber 8.7 starting from the test gas chamber 8.3 in which a water vapor volume flow of constant concentration flows which is supplied through the connectors 8.4. The water vapor concentration in the gas phase of the measuring chamber 8.7 is determined using the attenuation of the laser beam intensity due to an absorption by the water vapor molecules using a known, correspondingly adapted emission wavelength of the laser diode. The surface A permeable through the barrier element 8.5 by the water vapor in this respect corresponds to the corresponding open surface which is formed between the test gas chamber 8.3 and the measuring chamber 8.7 and through which the water vapor can permeate from the test gas chamber 8.3 into the measuring chamber 8.7. In the present case, the surface permeable by the water vapor amounts to approximately $1.347 \times 10^{-2}$ $m^2$. The laser diode spectrometer used for detecting the water vapor concentration in the measuring chamber 8.7 emits a laser beam which is led via a 2 m long optical path through the measuring chamber 8.7 designed as a multireflection measuring cell for 20irradiations. The laser diode spectrometer is furthermore designed such that a water vapor concentration can be detected in the range from 0.01 ppm to 1000 ppm.

The preconditioning of the measuring chamber 8.7 is carried out prior to carrying out a first measurement cycle comprising process steps (i) and (ii). In this respect, the measuring chamber 8.7 is purged by opening the valves 8.1 and 8.2 using a dry nitrogen purge gas volume flow ($\dot{V}$) free of water vapor of 55 sccm and is subsequently closed again by closing the valves.

The time concentration course of the permeate in the measuring chamber 8.7 can be understood with reference to FIG. 1d. On the carrying out of process step (i), the measuring chamber 8.7 is purged by opening the valves 8.2, 8.2 with a purge gas volume flow ($\dot{V}$) of the dry nitrogen purge gas set at 55 sccm on reaching an upper switchover concentration cvA fixed at 8.6 ppm until the lower switchover concentration cvS predefined at 28 ppm is reached. In this respect, a course of the water vapor concentration c in the gas phase of the measuring chamber 8.7 is recorded using the laser spectrometer, said course being specifically described by way of example as with the reference numeral 4 in FIG. 1b or with the same reference numeral in FIG. 1c and extending up to the reaching of the predefined lower switchover concentration cvS at 2.8 ppm starting from the predefined upper switchover concentration cvA at 8.6 ppm. In addition, the purge time tS is determined which is required up to the reaching of the lower switchover concentration cvS and which amounts to 30 minutes in the present case.

Due to the purge gas volume flow ($\dot{V}$) during the purge time tS of process step (i), the water vapor c concentration in the gas phase drops more in comparison with the concentration of the adsorbed water vapor than in the state of equilibrium (SOE) described by the system isotherm, whereby the SOE in the measuring chamber 8.7 is cancelled. In this respect, the concentrations of the adsorbed water vapor and of the gaseous water vapor follow the course marked by reference numeral 4 in FIG. 1a of a transient isotherm whose course depends on its start concentration at 8.6 ppm, on the wall covering at the start and on the purge gas volume ($\dot{V}$).

In the following process step (ii), the measuring chamber 8.7 is closed again by closing the valves 8.1 and 8.2 and the water vapor concentration is measured which increases again as a result of the continuous permeation through the barrier element 8.5. The water vapor concentration which increases in the measuring chamber 8.7 during process step (ii) can be understood by way of example by the reference numerals 5 and 6 in FIG. 1b and specifically in FIG. 1c. In this respect, starting from the predefined lower switchover concentration at 2.8 ppm, the enriching time tA up to the reaching of the predefined upper switchover concentration at 8.6 ppm, is determined.

The permeation rate can only be reliably determined when a stationary state has been adopted, with the test gas continuously permeating through the barrier element 8.5. In the named example, the presence of the stationary state was checked in that the measurement cycle comprising process steps (i) and (ii) was repeated until a coincidence of the total cycle time from the determined purge time tS and the determined enriching time tA of a measurement cycle with at least the total cycle time of a preceding measurement cycle was able to be determined with a maximum deviation of ±13%. The representation of FIG. 1c in particular illustrates this. While the enriching times and the purging times or the total cycle times and the determined permeation rates fluctuate a lot in the first 48 hours, after around 48 to 54 hours the stationary state is adopted, with the total cycle times of mutually following measurement cycles almost coinciding and with constant permeation rates being able to be determined.

In the present case, the determined enriching time tA amounts to 28:30 (hours:minutes) so that the permeation rate P of the barrier element 8.5 can be calculated using the enriching time tA determined from process step (ii) as well as the purge time tS determined from process step (i) and the course of the water vapor concentration c determined during the purge time tS by the equation $$P = \frac{\int (\varphi(t) \cdot \dot{V}) dt \cdot M \cdot p}{R \cdot T \cdot t_{total} \cdot A} \quad (1)$$

where $t_{total}$ is the sum of the purge time tS and the enriching time tA, M is the molar mass of the test gas (water vapor), p is the maintained pressure at 0.101325 MPa, R is the general gas constant and T is the temperature observed during process steps (i) and (ii). In the present case, the water vapor permeation rate of the barrier element 8,5 amounts to: $P = 3 \times 10^{-4}$ gm$^{-2}$d$^{-1}$.

To check the presence of the stationary state, the measurement cycle should be repeated in the permeation rate determination using the second measurement variant so frequently until the lower switchover concentration value cS of a measurement cycle coincides with the measurement cycle directly before it in time or differs from it by a maximum of twice the measurement uncertainty and simultaneously the difference between the upper switchover concentration value cA and the lower switchover concentration value cS agrees with the measurement cycle directly before it in time or differs from it by a maximum of twice the measurement uncertainty.

Independently of the first or second measurement variant, the presence of the stationary state can also be determined in that the measurement cycle is repeated until the respective determined permeation rate of a measurement cycle coincides with the permeation rate of at least one of the preceding measurement cycles or differs from it by a maximum of 20%.

To increase the measurement precision, the purge gas volume flow ($\dot{V}$) an be reduced. A reduction to 5 sccm would be conceivable, for example. For the first measurement variant, an improved measurement precision can be achieved in that the predefinable upper switchover concentration cvA is raised and the predefinable lower switchover concentration cvS is reduced so that the concentration difference between the two switchover concentrations becomes larger. For the second measurement variant, an improved measurement precision can be achieved by an extension of the predefinable purge time tvS and of the predefinable enriching time tvA.

With a further embodiment of the method in accordance with the invention, the use of a plurality of gas sensors is provided for the simultaneous determination of different simultaneously permeating test gases. There is, however, also the possibility of the use of multichannel gas sensors, for example of a UV, VIS, NIR, MIR, quantum cascade laser spectrometer or of a terahertz spectrometer with which a plurality of permeates can likewise be determined simultaneously.

The invention claimed is:
1. Method for determining the permeation rate of barrier materials,
   wherein in a measuring chamber (8.7) which has at least two shut-off elements (8.1; 8.2) for opening and closing, a concentration of at least one permeate is determined which, present as a test gas with a constant concentration in a test gas chamber (8.3), is permeated into the measuring chamber (8.7) through a barrier element (8.5) which is arranged between the test gas chamber (8.3) and the measuring chamber (8.7) and which has a known permeable surface (A);
   wherein
   in a process step (i),
   the measuring chamber (8.7) is purged with a constant permeate-free purge gas volume flow ($\dot{V}$) by opening the shut-off elements (8.1; 8.2) once a predefinable upper switchover concentration (cvA) has been reached in a first measurement variant or once a predefinable enriching time (tvA) has been reached in the second measuring variant; wherein the permeate concentration (c) in the open measuring chamber (8.7) drops as a result of the purging; and
   the time course of this permeate concentration (c) is either determined up to the reaching of a predefinable lower switchover concentration (cvS) in the first measurement variant, with a purge time (tS) being determined in this respect,
   or
   up to the reaching of a predefinable purge time (tvS) in the second measurement variant;
   and
   in a process step (ii),
   on reaching the predefinable lower switchover concentration (cvS) in the first measurement variant or
   on reaching the predefinable purge time (tvS) in the second measurement variant,
   the measuring chamber (8.7) is closed by closing the shut-off elements (8.1; 8.2), with the permeate concen- tration (c) increasing in the closed measuring chamber (8.7) as a result of the permeation, with an enriching time (tA) up to the reaching of the predefinable upper switchover concentration (cvA) being determined in the first measurement variant; and subsequently using the enriching time (tA) and using the purge time (tS) determined in process step (i) using the first measurement variant and using the course of the permeate concentration (c) determined during the purge time (tS), or the course of the permeate concentration (c) during the predefinable purge time (tvS) being determined in the process step (i) of the second measurement variant, the predefinable purge time (tvS) and the predefinable enriching time (tvA), the permeation rate (P) of the barrier element (8.5) is calculated using the equation $$P = \frac{\int (c(t) \cdot \dot{V}) dt \cdot M \cdot p}{R \cdot T \cdot t_{total} \cdot A}$$

where $t_{total}$ is the sum of the purge time (tS) and of the enriching time (tA) for the first measurement variant and is the sum of the predefinable purge time (tvS) and of the predefinable enriching time (tvA) for the second measurement variant; M is the molar mass of the permeate; p is the maintained pressure, R is the general gas constant; and T is the temperature maintained during process steps (i) and (ii).

2. A method in accordance with claim 1, characterized in that the method is carried out starting with process step (i) or with process step (ii).

3. A method in accordance with claim 1, characterized in that the permeation rate (P) is respectively determined from at least one measurement cycle respectively comprising at least one process step (i) and at least one process step (ii).

4. A method in accordance with claim 3, characterized in that in the second measurement variant, an upper switchover concentration value (cA) is adopted at the end of the predefinable enriching time (tvA) and a lower switchover concentration value (cS) is adopted at the end of the predefinable purge time (tvS).

5. A method in accordance with claim 4, characterized in that the measurement cycle is repeated until the lower switchover concentration (cS) coincides with the lower switchover concentration value of the measurement cycle directly before it in time or differs from it by a maximum of twice the measurement uncertainty and simultaneously the difference between the upper switchover concentration value (cA) and the lower switchover concentration value (cS) coincides with that of the measurement cycle directly before it in time or differs from it by a maximum of twice the measurement uncertainty.

6. A method in accordance with claim 1, characterized in that the measurement cycle is repeated in the first measurement variant until the total cycle time resulting from the sum of the enriching time (tA) and the purge time (tS) coincides with that of the measurement cycle directly before it in time or differs from it by a maximum of twice the measurement uncertainty.

7. A method in accordance with claim 1, characterized in that the measurement cycle is repeated until the respective determined permeation rate of a measurement cycle coincides with the permeation rate of at least one preceding measurement cycle or differs from it by a maximum of 20%.

8. A method in accordance with claim 1, characterized in that the measuring chamber (8.7) is prepurged with the permeate-free purge gas volume flow($\dot{V}$) at least once prior to carrying out the first measurement cycle by opening the shut-off elements (8.1; 8.2) and the measuring chamber (8.7) is subsequently closed again by closing the shut-off elements (8.1; 8.2) and remains closed sufficiently long until a state of equilibrium is reached in the measuring chamber (8.7).

9. A method in accordance with claim 1, characterized in that a non-invasive, optical and/or capacitive measuring method (8.6) is used for determining the permeate concentration and/or the change in the permeate concentration in the gas phase of the measuring chamber (8.7).

10. A method in accordance with claim 9. characterized in that a UV, VIS, NIR, MIR, quantum cascade laser spectrometer, a cavity ring-down spectrometer or a terahertz spectrometer is used as the measuring method.

11. A method in accordance with claim 9, characterized in that a laser-based measuring process, is used which uses at least one laser beam having an emission wavelength coordinated to the permeate(s) to be detected.

12. A method in accordance with claim 1, characterized in that condensable gases and vapors, preferably water vapor, is/are used as the test gas.

* * * * *